(12) United States Patent
Hilpert et al.

(10) Patent No.: US 8,436,205 B2
(45) Date of Patent: May 7, 2013

(54) TETRAHYDRONAPHTHALENE COMPOUNDS

(75) Inventors: Kurt Hilpert, Allschwil (CH); Francis Hubler, Allschwil (CH); Dorte Renneberg, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/125,848

(22) PCT Filed: Oct. 22, 2009

(86) PCT No.: PCT/IB2009/054668
§ 371 (c)(1),
(2), (4) Date: Apr. 25, 2011

(87) PCT Pub. No.: WO2010/046869
PCT Pub. Date: Apr. 29, 2010

(65) Prior Publication Data
US 2011/0207815 A1 Aug. 25, 2011

(30) Foreign Application Priority Data

Oct. 23, 2008 (WO) .................. PCT/IB2008/054376

(51) Int. Cl.
*C07C 211/00* (2006.01)
*C07C 13/48* (2006.01)
*C07C 309/00* (2006.01)

(52) U.S. Cl.
USPC ............................... 562/49; 564/372; 585/26

(58) Field of Classification Search .................... 562/49; 564/372; 585/26
See application file for complete search history.

(56) References Cited

U.S. PATENT DOCUMENTS

| 4,808,605 | A | | 2/1989 | Branca et al. | |
|---|---|---|---|---|---|
| 5,075,333 | A | * | 12/1991 | Bryce et al. | 514/481 |
| 5,407,897 | A | * | 4/1995 | Cary et al. | 504/108 |
| 6,608,097 | B2 | * | 8/2003 | Druzgala et al. | 514/394 |
| 8,202,885 | B2 | | 6/2012 | Hilpert et al. | |
| 2003/0130330 | A1 | | 7/2003 | Druzgala et al. | |
| 2011/0039905 | A1 | | 2/2011 | Hubler et al. | |
| 2011/0263648 | A1 | | 10/2011 | Hilpert et al. | |

FOREIGN PATENT DOCUMENTS

| WO | WO 2008/132679 | 11/2008 |
|---|---|---|
| WO | WO 2009/130679 | 10/2009 |

OTHER PUBLICATIONS

Hara et al. Tetrahydronaphthalene lignan compounds are potent anti-HIV type 1 agents. AIDS Research and Human Retroviruses. vol. 13, No. 8, 1997.*
Cimetiere et al. Synthesis and biological evaluation of new tetrahydronaphthalene derivatives as thromboxane receptor antagonists. Bioorganic & Medicinal Chemistry Letters, 8, 1375-1380, 1998.*
Kligfield et al. A model of graded ischemia in the isolated perfused rat heart. Journal of Applied Pathology, vol. 40, No. 6, Jun. 1976.*
Skrzypiec-Spring et al. Appraisal of state-of-the-art: Isolated heart perfusion to Langendorff-still viable to the new millenium. Journal of Pharmacological and Toxicological Methods, 55, 2007, 113-126.*
PCT/IB2009/054668 Written Opinion, Actelion Pharmaceuticals Ltd.
Clozel, J-P., et al., "Voltage-Gated T-Type $Ca^2$ Channels and Heart Failure", Proceedings of the Association of American Physicians, vol. 1 1 1, pp. 429-437, (1999).
du Souich, P., et al., "Nonlinear Kinetics and Pharmacologic Response to Mibefradil", Clinical Pharmacol Ther, vol. 67, pp. 249-257, (2000).
Honda, M., et al., "Divergent Renal Vasodilator Action of L- and T-type Calcium Antagonists in vivo", Journal of Hypertension, vol. 19, pp. 2031-2037, (2001).
Ramires, F.J.A., et al., "Myocardial Fibrosis Associated with Aldosterone or Angiotensin II Administration: Attenuation by Calcium Channel Blockade", J. Mol. Cell. Cardiol., vol. 30, pp. 475-483, (1998).
Villame, J., et al, "Effects of Mibefradil, a T- and L-Type Calcium Channel Blocker, on Cardiac Remodeling in the UM-X7.1 Cardiomyopathic Hamster", Cardiovascular Drugs and Therapy, vol. 15, pp. 41-48, (2001).
Wandel, C., et al., "Miberfradil is a P-Glycoprotein Substrate and a Potent Inhibitor of Both P-Glycoprotein and CYP3A in Vitro", Drug Metabolism and Disposition, vol. 28, No. 8, pp. 895-898, (2000).

* cited by examiner

Primary Examiner — Anna Pagonakis
(74) Attorney, Agent, or Firm — Hoxie & Associates, LLC.

(57) ABSTRACT

The invention relates to compounds of Formula (I) wherein $R^1$, $R^2$, $R^3$, $R^4$, $R^5$, m and n are as defined in the description, and to pharmaceutically acceptable salts of such compounds. These compounds are useful as calcium channel blockers.

Formula (I)

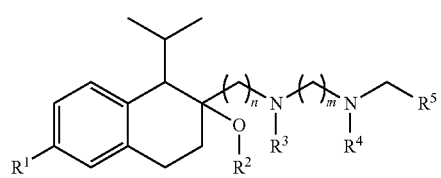

11 Claims, No Drawings

TETRAHYDRONAPHTHALENE COMPOUNDS

CROSS REFERENCE TO RELATED APPLICATIONS

This application is a US filing under 35 USC 371 of PCT/IB2009/054668 filed on Oct. 22, 2009, which claims the benefit of Application No. PCT/IB2008/054376 filed on Oct. 23, 2008, the contents of each of which are incorporated herein by reference.

The present invention relates to novel tetrahydronaphthalene compounds and their use as potent calcium channel blockers in the treatment or prevention of chronic stable angina, hypertension, ischemia (renal and cardiac), cardiac arrhythmias including atrial fibrillation, cardiac hypertrophy, or congestive heart failure, to pharmaceutical compositions containing these derivatives and to processes for their preparation. The bridged six-membered ring compounds derivatives of the present invention may also be used, alone or in pharmaceutical compositions, for the treatment of renal diseases, diabetes and its complications, hyperaldosteronism, epilepsy, neuropathic pain, or cancer in humans and other mammals.

Many cardiovascular disorders have been associated with a 'calcium overload' resulting from an abnormal elevated calcium influx through the plasma membrane of cardiac and vascular smooth muscle cells. There are 3 major pathways through which extracellular calcium can enter these cells: 1) receptor-activated calcium channels, 2) ligand-gated calcium channels and 3) voltage-operated calcium channels (VOCs).

VOCs have been classified into 6 main categories: L (Long-lasting), T (Transient), N (Neuronal), P (Purkinje cells), Q (after P) and R (Remaining or Resistant).

L-type calcium channels are responsible for the inward movement of calcium that initiates contraction in cardiac and smooth muscle cells suggesting a putative application for blockers of these channels in the cardiovascular field. In this view, L-type calcium channel blockers have been used in clinic since the early 60s and are now recommended as a first line of treatment for systolic-diastolic hypertension and angina pectoris.

T-type calcium channels are found in various tissues such as coronary and peripheral vasculature, sinoatrial node and Purkinje fibres, brain, adrenal glands and in the kidney. This broad distribution suggests a T-type channel blocker to have a putative cardiovascular protection, to have en effect on sleep disorders, mood disorders, depression, migraine, hyperaldosteroneemia, preterm labor, urinary incontinence, brain aging or neurodegenerative disorders such as Alzheimers disease.

Mibefradil (Posicor®), the first L-type and T-type calcium channels blocker demonstrated a superior effect over calcium channel blockers, which target the L channel predominantly.

Mibefradil was used for the treatment of hypertension and angina without showing negative side-effects often seen by L channel blockers like inotropy, reflex tachycardia, vasoconstrictive hormone release or peripheral edema. Additionally, mibefradil showed a potentially cardioprotective effect (Villame, Cardiovascular Drugs and Therapy 15, 41-28, 2001; Ramires, J Mol Cell Cardiol 1998, 30, 475-83), a renal protective effect (Honda, Hypertension 19, 2031-37, 2001), and showed a positive effect in the treatment of heart failure (Clozel, Proceedings Association American Physicians 1999, 111, 429-37).

Despite the enormous demand for a compound of this profile, mibefradil was withdrawn from the market in 1998 (one year after its launch), due to unacceptable CYP 3A4 drug interactions. Moreover, ECG abnormalities (i.e. QT prolongations) and interaction with the MDR-1 mediated digoxin efflux were also reported (du Souich, Clin Pharmacol Ther 67, 249-57, 2000; Wandel, Drug Metab Dispos 2000, 28, 895-8).

The compounds of the present invention are potent T/L channel blockers and therefore useful in diseases where both, T and L channels are involved.

Various embodiments of the invention are presented hereafter:

1) A first embodiment of the invention relates to the compounds of formula (I)

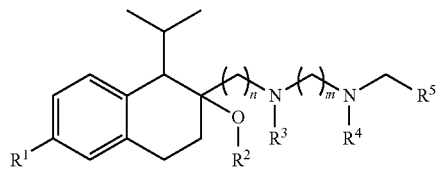

Formula (I)

wherein
$R^1$ represents hydrogen or fluorine;
$R^2$ represents hydrogen, or —CO—$R^{21}$;
$R^{21}$ represents $(C_{1-5})$alkyl, $(C_{1-3})$fluoroalkyl, $(C_{3-6})$cycloalkyl, $(C_{3-6})$cycloalkyl-$(C_{1-3})$alkyl, $(C_{1-5})$alkoxy, $(C_{1-2})$alkoxy-$(C_{1-3})$alkyl, or $R^{22}R^{23}N$—;
$R^{22}$ represents $(C_{1-5})$alkyl;
$R^{23}$ represents hydrogen, or $(C_{1-5})$alkyl;
n represents the integer 1, 2, 3, or 4;
m represents the integer 2, 3, 4, or 5;
$R^3$ represents hydrogen, $(C_{1-5})$alkyl, or $(C_{1-3})$fluoroalkyl;
$R^4$ represents $(C_{1-3})$fluoroalkyl which is optionally mono-substituted with phenyl;
$R^5$ represents $(C_{1-5})$alkyl, which is unsubstituted, mono-, or di-substituted, wherein each substituent is independently selected from the group consisting of hydroxy, $(C_{1-2})$alkoxy, $(C_{1-2})$alkoxy-$(C_{1-3})$alkoxy, hydroxy-$(C_{2-4})$alkoxy, aryl-$(C_{1-3})$alkoxy, and aryl-$(C_{1-2})$alkoxy-$(C_{1-3})$alkoxy;
or $R^5$ represents $(C_{1-5})$alkyl, which is di-substituted, wherein one substituent is $(C_{1-2})$alkoxy and the other is phenyl;
or $R^5$ represents a saturated four- to eight-membered carbon ring optionally containing two oxygen ring atoms, whereby the two oxygen ring atoms are not adjacent to each other.

The following paragraphs provide definitions of the various chemical moieties for the compounds according to the invention and are intended to apply uniformly throughout the specification and claims, unless an otherwise expressly set out definition provides a broader or narrower definition.

The term "$(C_{1-5})$alkyl" means a straight-chain or branched-chain alkyl group with 1 to 5 carbon atoms. Preferred are groups with 1 to 4 carbon atoms. The term "$(C_{x-y})$alkyl" (x and y being an integer) refers to a straight or branched chain alkyl group containing x to y carbon atoms. Examples of $(C_{1-5})$alkyl groups are methyl, ethyl, n-propyl, isopropyl, n-butyl, sec.-butyl, tert.-butyl, isobutyl, n-pentyl, and isopentyl. Preferred are methyl, ethyl, n-propyl, and isopropyl. Most preferred is methyl. For the substituent $R^{21}$ a preferred example of a $(C_{1-5})$alkyl group is isopropyl.

Preferred examples of $R^5$ representing unsubstituted $(C_{1-5})$alkyl are isopropyl and tert.-butyl. In preferred examples of $R^5$ representing "$(C_{1-5})$alkyl, which is mono-, or di-substituted, wherein each substituent is independently selected from the group consisting of hydroxy, $(C_{1-2})$alkoxy, $(C_{1-2})$alkoxy-$(C_{1-3})$alkoxy, hydroxy-$(C_{2-4})$alkoxy, aryl-$(C_{1-3})$alkoxy, and aryl-$(C_{1-2})$alkoxy-$(C_{1-3})$alkoxy" the substituent(s) is/are selected from hydroxy, $(C_{1-2})$alkoxy, $(C_{1-2})$alkoxy-$(C_{1-3})$alkoxy, and hydroxy-$(C_{2-4})$alkoxy (especially from $(C_{1-2})$alkoxy). Particular examples of such groups are 1,3-dimethoxy-2-methyl-propane-2-yl, 2-methoxy-propane-2-yl and 1,1-dimethyl-2-methoxy-ethyl-1-yl, especially 1,3-dimethoxy-2-methyl-propane-2-yl.

A preferred example of $R^5$ representing "$(C_{1-5})$alkyl, which is di-substituted, wherein one substituent is $(C_{1-2})$ alkoxy and the other is phenyl" is 1-methoxy-1-phenyl-ethan-1-yl.

The term "$(C_{1-5})$alkoxy" means a group of the formula $(C_{1-5})$alkyl-O— in which the term $(C_{1-5})$alkyl has the previously given significance. The term "$(C_{x-y})$alkoxy" (x and y being an integer) refers to a straight or branched chain alkoxy group containing x to y carbon atoms. Examples of $(C_{1-5})$ alkoxy groups are methoxy, ethoxy, n-propoxy, isopropoxy, n-butoxy, isobutoxy, sec-butoxy and tert.-butoxy. Preferred are methoxy and ethoxy.

Preferred examples of $R^5$ representing "a saturated four- to eight-membered carbon ring optionally containing two oxygen ring atoms, whereby the two oxygen ring atoms are not adjacent to each other" are 1,3-dioxolan-2-yl, and 1,3-dioxan-2-yl.

The term "$(C_{1-3})$fluoroalkyl" means a straight-chain or branched-chain $(C_{1-3})$alkyl group which is substituted with 1 to 7 fluorine atoms. Likewise, the term "$(C_{x-y})$fluoroalkyl" (x and y being an integer) means a straight-chain or branched-chain $(C_{x-y})$alkyl group which is substituted with 1 up to the maximum number of fluorine atoms. Examples of $(C_{1-3})$fluoroalkyl groups are trifluoromethyl, 2-fluoroethyl, 2,2-difluoroethyl, 2,2,2-trifluoroethyl, and pentafluoroethyl. Preferred are trifluoromethyl, 2,2,2-trifluoroethyl, and pentafluoroethyl. Most preferred are (especially) trifluoromethyl and 2,2,2-trifluoroethyl. For the substituent $R^{21}$, 2-fluoroethyl and, notably, 2,2,2-trifluoroethyl are preferred. For the substituent $R^3$, 2-fluoroethyl, 2,2-difluoroethyl and 2,2,2-trifluoroethyl are preferred. For the substituent $R^4$, 2-fluoroethyl, 2,2-difluoroethyl and 2,2,2-trifluoroethyl are preferred.

The term "$(C_{1-3})$fluoroalkyl which is optionally mono-substituted with phenyl" means a $(C_{1-3})$fluoroalkyl group as defined before wherein one hydrogen or fluorine atom is replaced by a phenyl group. Examples of $R^4$ representing such a group are 1-phenyl-2,2,2-trifluoroethyl, 2-fluoroethyl, 2,2-difluoroethyl and 2,2,2-trifluoroethyl. Preferred are unsubstituted $(C_{1-3})$fluoroalkyl groups such as 2-fluoroethyl, 2,2-difluoroethyl and 2,2,2-trifluoroethyl.

The term "$(C_{3-6})$cycloalkyl" means a saturated cyclic alkyl group with 3 to 6 carbon atoms. Examples of $(C_{3-6})$cycloalkyl groups are cyclopropyl, cyclobutyl, cyclopentyl and cyclohexyl. Preferred is cyclopropyl.

The term "$(C_{3-6})$cycloalkyl-$(C_{1-3})$alkyl" means a $(C_{3-6})$ cycloalkyl group as defined before which is attached to the rest of the molecule via a $(C_{1-3})$alkyl group as defined before. Examples are cyclopropyl-methyl, cyclopentyl-methyl and cyclohexyl-methyl; preferred is cyclopropyl-methyl.

The term "$(C_{1-2})$alkoxy-$(C_{1-3})$alkyl" means a $(C_{1-2})$ alkoxy-group as defined before which is attached to the rest of the molecule via a $(C_{1-3})$alkyl group as defined before. Examples are methoxymethyl, 2-methoxy-ethyl, 2-methoxy-2-methyl-ethyl and 3-methoxy-propyl. For the substituent $R^{21}$, 2-methoxy-2-methyl-ethyl and especially methoxymethyl are preferred.

An example of a "$(C_{1-2})$alkoxy-$(C_{1-3})$alkoxy" group is 2-methoxy-ethoxy.

An example of a "hydroxy-$(C_{2-4})$alkoxy" group is 2-hydroxy-ethoxy.

An example of a "aryl-$(C_{1-3})$alkoxy" group is benzyloxy.

An example of a "aryl-$(C_{1-2})$alkoxy-$(C_{1-3})$alkoxy" group is 2-benzyloxy-ethoxy.

The term "halogen" means fluorine, chlorine, bromine or iodine, especially fluorine or chlorine.

The term "aryl" means a phenyl group. The aryl group may be unsubstituted (preferred) or mono-, di-, or tri-substituted wherein the substituents are independently selected from the group consisting of $(C_{1-4})$alkyl, $(C_{1-4})$alkoxy, halogen, trifluoromethyl, and trifluoromethoxy.

In the following, further embodiments of the invention are described:

2) A further embodiment of the invention relates to compounds of formula (I) according to embodiment 1), wherein the configuration of the tetrahydronaphthalene moiety is such that the $R^2$—O— substituent and the isopropyl substituent of the tetrahydronaphthalene moiety are in cis relation (i.e. the absolute configuration is as depicted in either formula ($I_{E1}$) or formula ($I_{E2}$) below).

3) A further embodiment of the invention relates to compounds of formula (I) according to embodiments 1), or 2), wherein the absolute configuration is as depicted in formula ($I_{E1}$)

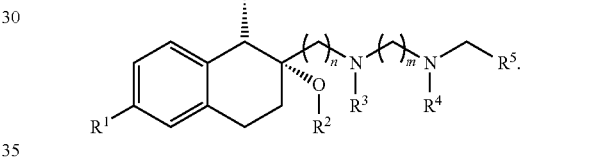

($I_{E1}$)

4) A further embodiment of the invention relates to compounds of formula (I) according to embodiments 1), or 2), wherein the absolute configuration depicted is as in formula ($I_{E2}$)

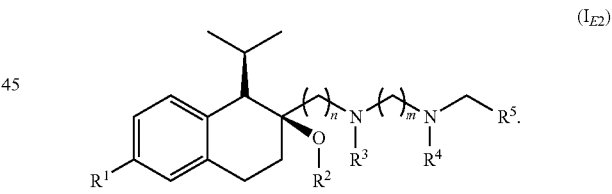

($I_{E2}$)

5) A further embodiment of the invention relates to compounds of formula (I) according to any one of embodiments 1) to 4), wherein $R^1$ represents fluorine.

6) A further embodiment of the invention relates to compounds of formula (I) according to any one of embodiments 1) to 5), wherein $R^2$ represents —CO—$R^{21}$; and $R^{21}$ represents $(C_{1-5})$alkyl, $(C_{1-3})$fluoroalkyl, or $(C_{3-6})$cycloalkyl.

7) A further embodiment of the invention relates to compounds of formula (I) according to any one of embodiments 1) to 6), wherein $R^{21}$ represents $(C_{1-5})$alkyl (preferred), or $(C_{1-3})$fluoroalkyl.

8) A further embodiment of the invention relates to compounds of formula (I) according to any one of embodiments 1) to 5), wherein $R^2$ represents hydrogen.

9) A further embodiment of the invention relates to compounds of formula (I) according to any one of embodiments 1) to 8), wherein m represents the integer 2 or 3.

10) A further embodiment of the invention relates to compounds of formula (I) according to any one of embodiments 1) to 9), wherein m represents the integer 3.

11) A further embodiment of the invention relates to compounds of formula (I) according to any one of embodiments 1) to 10), wherein n represents the integer 2.

12) A further embodiment of the invention relates to compounds of formula (I) according to any one of embodiments 1) to 11), wherein $R^3$ represents $(C_{1-4})$alkyl (notably methyl).

13) A further embodiment of the invention relates to compounds of formula (I) according to any one of embodiments 1) to 12), wherein $R^4$ represents unsubstituted $(C_{1-3})$fluoroalkyl.

14) A further embodiment of the invention relates to compounds of formula (I) according to any one of embodiments 1) to 13), wherein $R^5$ represents $(C_{1-5})$alkyl, which is unsubstituted, mono-, or di-substituted, wherein each substituent is independently selected from the group consisting of hydroxy, $(C_{1-2})$alkoxy, $(C_{1-2})$alkoxy-$(C_{1-3})$alkoxy, and hydroxy-$(C_{2-4})$alkoxy;
or $R^5$ represents a saturated four- to eight-membered carbon ring containing two oxygen ring atoms, whereby the two oxygen ring atoms are not adjacent to each other.

15) A further embodiment of the invention relates to compounds of formula (I) according to any one of embodiments 1) to 13), wherein $R^5$ represents $(C_{1-5})$alkyl, which is unsubstituted, mono-, or di-substituted, wherein each substituent is independently selected from $(C_{1-2})$alkoxy.

16) A further embodiment of the invention relates to compounds of formula (I) according to any one of embodiments 1) to 13), wherein $R^5$ represents $(C_{1-5})$alkyl, which is di-substituted, wherein each substituent is independently selected from $(C_{1-2})$alkoxy (preferably both substituents are methoxy).

17) A further embodiment of the invention relates to compounds of formula (I) according to embodiment 1) which are also compounds of formula $(I_{CE})$

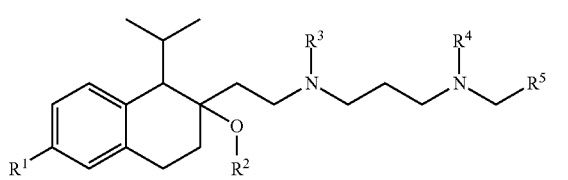

Formula $(I_{CE})$ wherein
$R^1$ represents fluorine;
$R^2$ represents hydrogen, or —CO—$R^{21}$;
$R^{21}$ represents $(C_{1-5})$alkyl, or $(C_{1-3})$fluoroalkyl;
$R^3$ represents $(C_{1-5})$alkyl;
$R^4$ represents $(C_{2-3})$fluoroalkyl;
$R^5$ represents $(C_{1-5})$alkyl, which is unsubstituted, mono-, or (preferably) di-substituted, wherein each substituent is independently selected from $(C_{1-2})$alkoxy.

The present invention also includes isotopically, especially $^2$H (deuterium) labelled compounds of formula (I) which compounds are identical to the compound of formula (I) wherein one or more atoms have been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting eg. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or labelled with one or more deuterium atoms. In a sub-embodiment, the compounds of formula (I) are not isotopically labelled. Isotopically labelled compounds of formula (I) may be prepared in analogy to the methods described hereinafter, but using the appropriate isotopic variation of suitable reagents or starting materials.

The compounds of formula (I) contain stereogenic or asymmetric centers, such as asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formulae (I), $(I_{CE})$, $(I_{E1})$, and/or $(I_{E2})$ is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* 1986, 33, 201-217.

In one embodiment examples of preferred compounds of formula (I) are selected from the group consisting of:
(1S,2S)-6-Fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol;
Isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
3,3,3-Trifluoro-propionic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
Fluoro-acetic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
(1S,2S)-2-[2-({3-[(2,2-Difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-ol;
Isobutyric acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester;
3,3,3-Trifluoro-propionic acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester;
(1S,2S)-6-Fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-ol;
Isobutyric acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester; and 3,3,3-Trifluoro-propionic acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester.

The compounds of formulae (I), ($I_{CE}$), ($I_{E1}$), and/or ($I_{E2}$) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition 2005, Part 5, "Pharmaceutical Manufacturing" [published by Lippincott Williams & Wilkins]) by bringing the described compounds of formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I), or pharmaceutically acceptable salts thereof, are useful in the preparation of a medicament, and/or are suitable for the treatment or prevention of chronic stable angina, hypertension, ischemia (renal and cardiac), cardiac arrhythmias including atrial fibrillation, cardiac hypertrophy, or congestive heart failure.

The compounds of formula (I), or pharmaceutically acceptable salts thereof, are further also useful in the preparation of a medicament, and/or are suitable, for the following disease groups alone or in any combination:

for the treatment of renal diseases, diabetes and its complications, hyperaldosteronism, epilepsy, neuropathic pain, or cancer in humans and other mammals;

for use as anti-fibrillatory agent, anti-asthmatic agent, anti-atherosclerotic agent, additive to cardioplegic solutions for pulmonary bypasses, adjunct to thrombolytic therapy, as antiaggregant agent, or as agent for the treatment of unstable angina;

for the treatment or prophylaxis of hypertension, especially portal hypertension, hypertension secondary to treatment with erythropoietin and low renin hypertension;

for use in hypoxic or ischemic diseases, or as anti ischemic agent for the treatment of e.g. cardiac, renal and cerebral ischemia and reperfusion (e.g. occurring after cardiopulmonary bypass surgery), coronary and cerebral vasospasm and the like, therapy for peripheral vascular diseases (e.g. Raynaud's disease, intermittent claudication, Takayashus disease), sickle cell disease including initiation and/or evolution of the pain crisis;

for the treatment or prophylaxis of disorders related to renal, glomerular and mesangial cell function, including acute and chronic renal failure, diabetic nephropathy, hypertension-induced nephropathy, glomerular injury, renal damage related to age or dialysis, nephrosclerosis, nephrotoxicity related to imaging and contrast agent and to cyclosporine, renal ischemia, primary vesicoureteral reflux, or glomerulosclerosis;

for use in therapy for myocardial infarction, treatment of cardiac hypertrophy, primary and secondary pulmonary hypertension, therapy for congestive heart failure including inhibition of fibrosis, inhibition of left ventricular dilatation, remodelling and dysfunction, or restenosis following angioplasty or stenting;

for the treatment of endotoxemia or endotoxin shock, or hemorrrhagic shock;

for the treatment of sexual dysfunction in both men (erectile dysfunction e.g. due to diabetes mellitus, spinal cord injury, radical prostatectomy, psychogenic etiology and other causes) and women by improving blood flow to the genitalia, especially corpus cavernosum;

for the prevention and/or reduction of cancer or end-organ damage associated with cell proliferation;

for therapy of metabolic disorders or chronic inflammatory diseases, insulin-dependent and non insulin-dependent diabetes mellitus and their complications (e.g. neuropathy, retinopathy), hyperaldosteronism, bone remodelling, psoriasis, arthritis, rheumatoid arthritis, osteoarthritis sarcoidosis, or eczematous dermatitis;

for the treatment of hepatotoxicity and sudden death, early and advanced liver disease and injury including attendant complication (e.g. hepatotoxicity, fibrosis, cirrhosis), deleterious consequences of tumors such as hypertension resulting from hemangiopericytoma, spastic diseases of the urinary tract and/or bladder, hepatorenal syndrome, immunological diseases involving vasculitis such as lupus, systemic sclerosis, mixed cryoglobulinemia, fibrosis associated with renal dysfunction and hepatotoxicity;

for use in gastrointestinal diseases such as ulcerative colitis, Crohn's disease, gastric mucosal damage, ulcer inflammatory bowel disease and ischemic bowel disease, gall bladder or bile duct-based diseases such as cholangitis, pancratitis, regulation of cell growth, begning prostatic hypertrophy, or transplantation, or for use as anti-diarrheal agent;

for the treatment of disorders involving bronchoconstriction or disorders of chronic or acute inflammation such as obstructive pulmonary disease and adult distress syndrome;

for the alleviation of pain including neuropathic pain, peripheral pain and pain associated with cancer such as pain associated with prostate cancer or bone-cancer;

for the treatment of central nervous system vascular disorders such as stroke, transient ischemic attacks, migraine and subarachnoid hemorrhage, central nervous system behavioural disorders, treatment of dementia including Alzheimer's dementia, senile dementia and vascular dementia, epilepsy, or sleep disorders; or for reduction of general morbidity and/or mortality as a result of above utilities.

The present invention also relates to a method for the prevention or treatment of a disease or disorder mentioned herein comprising administering to a subject a pharmaceutically active amount of a compound of formula (I).

Furthermore, the compounds of the formula (I) may also be used favourably in combination with one or more agents selected from lipid lowering agents such as statins, anticoagulants such as coumarins, antithrombotic agents such as clopidogrel, β-blockers, and other cardioprotective agents.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formulae ($I_{CE}$), ($I_{E1}$), and/or ($I_{E2}$) and vice versa.

Preparation of Compounds of Formula (I):

Compounds of formula (I) can be prepared via intermediates (IV), (V) and (VI) following the procedures outlined in Scheme 1 below.

Compounds of formula (IV) wherein $R^2$ represents H can be prepared by reductive amination of aldehydes of formula (III) using amines of formula (II) under standard conditions such as NaBH$_3$CN as reducing reagent in a suitable solvent like a mixture of DCM and AcOH and preferably at temperatures between 0 and rt.

The amide bond in compounds of formula (IV) wherein R$^2$ represents H is reduced using standard conditions such as a solution of BH$_3$.THF complex in THF in a suitable solvent like THF, preferably at temperatures between 0° C. and 60° C. The resulting product of formula (V) wherein R$^2$ represents H are generally obtained as BH$_3$ complex and are treated with ethylene diamine in a protic solvent like MeOH preferably at temperatures between rt and 90° C. to isolate the free amine of formula (V) wherein R$^2$ represents H.

The secondary amine in compounds of formula (V) wherein R$^2$ represents H is acylated with a derivative of an acid R$^{4*}$—COOH, wherein R$^{4*}$ represents (C$_{1-2}$)fluoroalkyl, using for example the acid chloride or acid anhydride in a suitable solvent like DCM or THF in the presence of a base like DIPEA or pyridine and preferably at temperatures between 0 and rt to give compounds of formula (VI). In case, an acylation of the tertiary alcohol in compounds of formula (VI) occurred, an additional saponification step using standard conditions is necessary to isolate the compounds of formula (VI) wherein R$^2$ represents H.

The amide bond in compounds of formula (VI) wherein R$^2$ represents H is reduced using similar conditions as previously described for the preparation of compounds of formula (V) from compounds of formula (IV) to give compounds of formula (I).

In a variation, the secondary amine in compounds of formula (V) wherein R$^2$ represents H is directly alkylated to the compound of formula (I) using the appropriate alkylating reagent R$^4$—X wherein X is OTs, OMs, OTf, Cl or Br in the presence of a mineral or organic base like Cs$_2$CO$_3$ or DIPEA and in a suitable solvent like THF or DMF preferably at temperatures between rt and 150° C.

Alcohols of formula (I) wherein R$^2$ represents H can be acylated using standard reagents such as acid chlorides, acid anhydrides, chloroformates, isocyanates, or carbamoylchlorides, if necessary in presence of a Lewis acid such as MgBr$_2$, or in presence of a base such as NEt$_3$ in inert solvents such as DCM or THF at temperatures between 0° C. and rt to give compounds of formula (I) wherein R$^2$ represents —COR$^{21}$.

Alternatively, compounds of formula (I) wherein R$^2$ represents H can be prepared via intermediate (VIII) following the procedures outlined in Scheme 1 below.

Compounds of formula (VIII) wherein R$^2$ represents H are prepared by coupling the amine of formula (II) with the acid of formula (VII) using standard conditions like EDC and HOBt or PyBOP in the presence of a base like DIPEA and in a suitable solvent like DCM, THF or DMF, preferably at rt. Both amide bonds in compounds of formula (VIII) wherein R$^2$ represents H are reduced to give compound of formula (I) wherein R$^2$ represents H. The reducing procedure is similar to the one previously described for the preparation of compounds of formula (V) from compounds of formula (IV).

In another variation, compounds of formula (I) wherein R$^2$ represents H can be prepared via intermediates of formula (X) and (V) wherein R$^2$ represents H following the procedures outlined in Scheme 1 below.

Compounds of formula (X) wherein R$^2$ represents H are prepared by coupling the amine of formula (II) with the acid of formula (IX) using the standard conditions previously described for the preparation of compounds of formula (VIII). Both amide bonds in compounds of formula (X) wherein R$^2$ represents H are reduced to give the compound of formula (V) wherein R$^2$ represents H. The reducing procedure is similar to the one previously described for the preparation of compounds of formula (V) from compounds of formula (IV).

Scheme 1

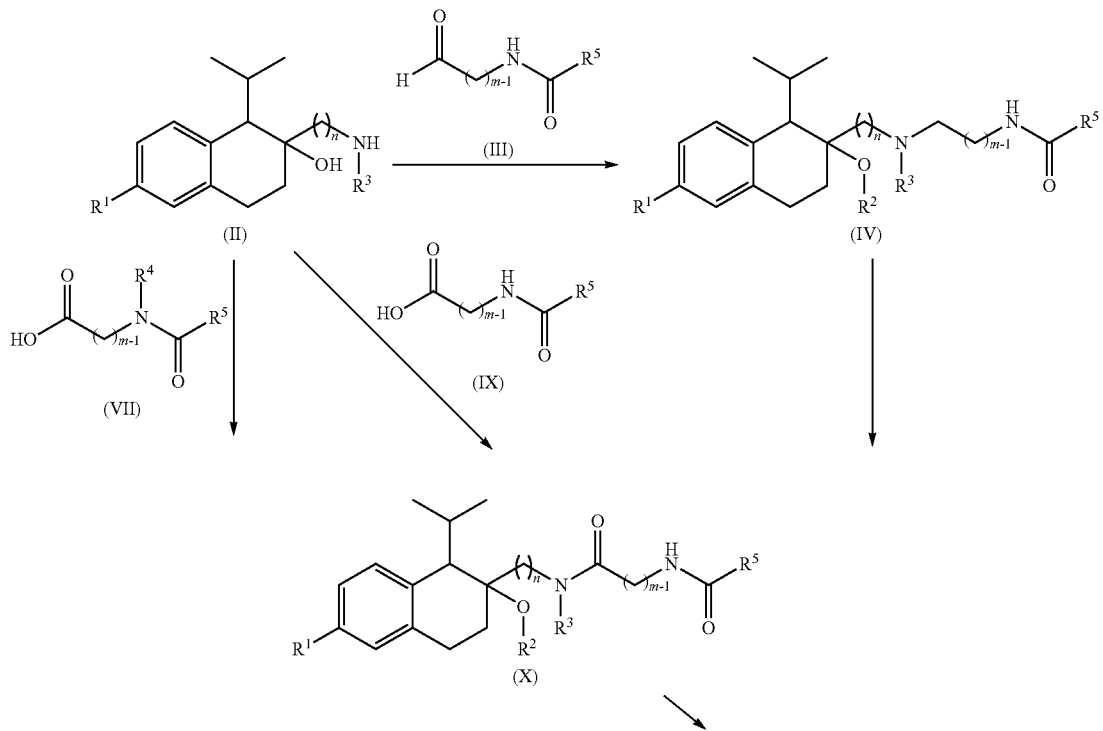

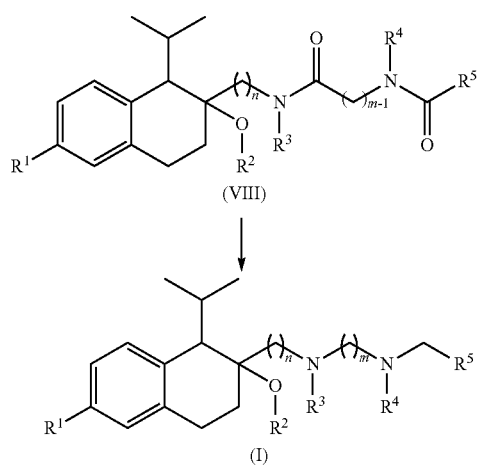
(VIII)

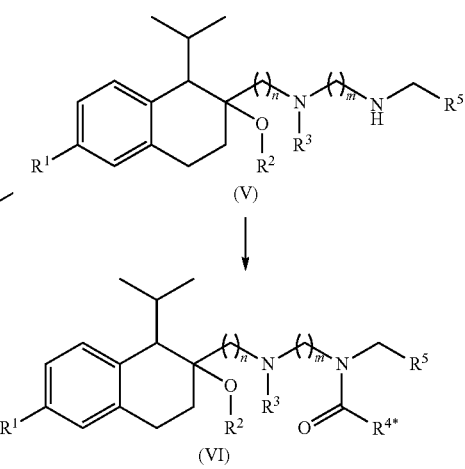
(V)

(I) ← (VI)

Compounds of formula (II) can be prepared following the procedures outlined in Scheme 2 below.

The compound of formula (XI) and the compounds of formula (XIV), wherein n=2, 3, 4 are prepared according to U.S. Pat. No. 4,680,310 and U.S. Pat. No. 4,808,605, or according to U.S. Pat. No. 5,120,759 and Tetrahedron: Assymmetry, 1997, 8 (21), 3617-3623, for the enantiomerically enriched compounds.

Compound of formula (XII) are prepared by hydrocyanation of the ketone of formula (XI) under standard conditions using e.g. KCN or TMSCN in appropriate solvents like MeCN or DCM. Consecutive reduction of the nitrile moiety in the compound of formula (XII) using standard reducing reagent like $LiAlH_4$ in a suitable solvent like THF gives compound of formula (XIII). The primary amine in the compound of formula (XIII) is alkylated using a reductive alkylation procedure with an appropriate commercially available aldehyde and $NaBH(OAc)_3$ or $NaBH_3CN$ as reducing reagent in a suitable solvent like a mixture of DCM and AcOH and preferably at temperatures between 0 and rt to give the compound of formula (II), wherein n=1. The alkylation can also be obtained using the appropriate alkylating reagent $R^3$—X wherein X is OTs, OMs, OTf, Cl or Br in a solvent like DMF and preferably at temperatures between rt and 100° C.

The primary alcohol group in compounds of formula (XIV) is transformed into a leaving group $L^1$ wherein $L^1$ is OTs, OMs, OTf, Cl or Br, using well known methods such as Ts—Cl in presence of bases such as $NEt_3$, DMAP, and in an adequate solvent such as toluene. Treatment of compounds of formula (XV) with the appropriate amine $R^3$—$NH_2$ if necessary in presence of a base such as DIPEA at temperatures between rt and 110° C. gives compounds of formula (II).

Scheme 2

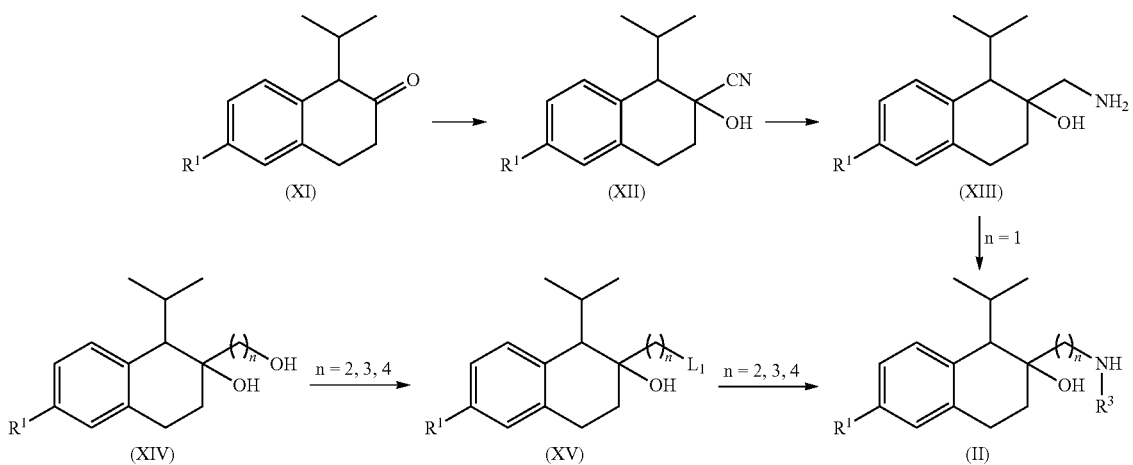

Compounds of formula (III) can be prepared following the procedures outlined in Scheme 3 below.

A commercially available alkylamine derivative of formula (XVI) is coupled to the appropriate acid of formula (XVII), which is commercially available, using standard amide coupling reagents and conditions such as EDC/HOBt in presence of a base such as DIPEA, in solvents like THF at rt to give the amide of formula (XVIII). Hydrolysis of the acetal using standard acidic conditions such as TsOH in acetone at rt leads to the desired aldehyde of formula (III).

Scheme 3

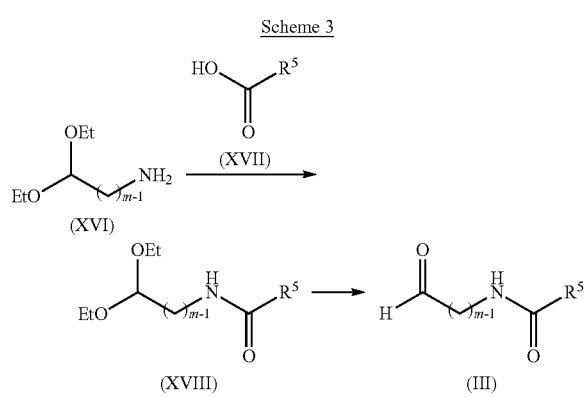

Compounds of formula (VII) can be prepared following the procedures outlined in Scheme 4 below.

Compounds of formula (XXI) wherein $R^4$ is optionally mono-substituted with phenyl are prepared from commercially available amines of formula (XX) according to known procedures (WO2005021487 and J. Org. Chem., 2006, 71, 4320-4323). The secondary amine in compounds of formula (XXI) is coupled to the appropriate acid of formula (XXII), which is commercially available, to give the amide compound of formula (XXIII). A similar activation of the acid of formula (XXII) is used as previously described for the preparation of the compound of formula (XVIII) or acids of formula (XXII) are activated as acid chlorides according to known procedures. The methyl ester moiety in compounds of formula (XXIII), are saponified using standard basic conditions such as LiOH or NaOH in solvents like EtOH, THF or $H_2O$ at rt to give compounds of formula (VII).

Compounds of formula (IX) can be prepared following the procedures outlined in Scheme 4 below.

A commercially available amine of formula (XX) is coupled to the appropriate acid of formula (XXII), which is commercially available, to give the amide compound of formula (XXIV). A similar coupling procedure is used as previously described for the preparation of the compound of formula (XVIII). The methyl ester moiety in compounds of formula (XXIV), is saponified as previously described for compounds of formula (XXIII).

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as $NEt_3$, diethylamine) and eluent B (hexane), at a flow rate of 0.8 to 150 mL/min.

Experimental Part

The following examples illustrate the invention but do not at all limit the scope thereof.

All temperatures are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, q=quartett, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 µm, gradient: 10-95%

Scheme 4

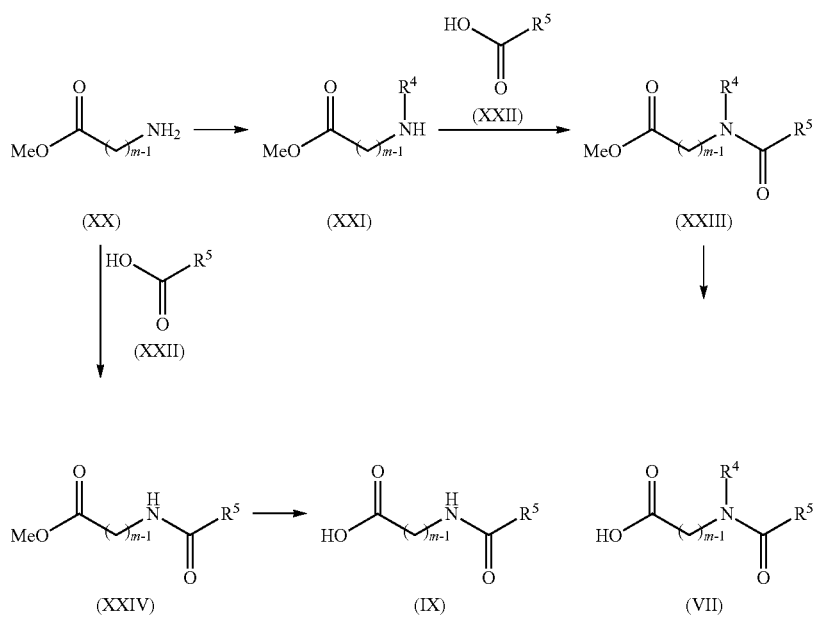

acetonitrile in water containing 0.5% of formic acid) or by column chromatography on silica gel.

Abbreviations: (as used herein and in the description above)

| | |
|---|---|
| Ac | acetyl |
| anh. | anhydrous |
| BSA | bovine serum albumin |
| CC | column chromatography on silica gel |
| DCM | dichloromethane |
| DIPEA | diisopropyl-ethylamine, Hünig's base, ethyl-diisopropylamine |
| DMAP | dimethylaminopyridine |
| DMF | dimethylformamide |
| DMSO | dimethylsulfoxide |
| EDC | N-(3-dimethylaminopropyl)-N'-ethylcarbodiimide |
| Et | ethyl |
| EtOAc | ethyl acetate |
| EtOH | ethanol |
| h | hour(s) |
| Hept | heptane |
| HOBt | 1-hydroxybenzotriazole |
| HPLC | high performance liquid chromatography |
| LC-MS | liquid chromatography-mass spectrometry |
| Me | methyl |
| MeCN | acetonitrile |
| MeOH | methanol |
| min | minute(s) |
| Ms | methanesulfonyl (such as in Ms—Cl = methanesulfonylchloride) |
| $NEt_3$ | triethylamine |
| PyBOP | benzotriazole-1-yl-oxy-tris-pyrrolidino-phosphonium hexafluorophosphate |
| sat. | saturated |
| tert.- | tertiary (such as in tert.-butyl = t-butyl = tertiary butyl) |
| THF | tetrahydrofuran |
| TLC | thin layer chromatography |
| rt | room temperature |
| $t_R$ | retention time |
| Tf | trifluoromethanesulfonyl (such as in OTf = trifluoromethanesulfonyloxy) |
| Ts | para-toluenesulfonyl (such as in Ts—Cl = para-toluenesulfonylchloride) |
| TsOH | para-toluenesulfonic acid |

PREPARATION OF EXAMPLES

Example 1

(1S,2S)-6-Fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol 1.1 N-(3,3-Diethoxy-propyl)-3-methoxy-2-methoxymethyl-2-methyl-propionamide 5 g of 3-methoxy-2-methoxymethyl-2-methyl-propionic acid (prepared as described in EP609058) were dissolved in 49 mL of DCM and 12 mL of THF. 11.4 mL of DIPEA, 5.84 g of HOBt, 7.07 g of EDC and 5.45 g of 3,3-diethoxy-propylamine were added sequentially. The mixture was stirred for 23 h at rt, diluted with DCM and washed with sat. $NaHCO_3$. The organic phase was dried over anh. $Na_2SO_4$ and concentrated in vacuo. The resulting crude material was purified by CC using Hept/EtOAc from 3/1 to 0/1 as eluant to yield 7.25 g of N-(3,3-diethoxy-propyl)-3-methoxy-2-methoxymethyl-2-methyl-propionamide as a yellowish oil.

$^1$H-NMR ($CDCl_3$): 7.04 (s, 1H), 4.51 (t, 1H), 3.45-3.7 (m, 4H), 3.43 (s, 4H), 3.32 (s, 6H), 3.30 (dd, 2H), 1.79 (dd, 2H), 1.19 (t, 6H), 1.12 (s, 3H).

1.2 3-methoxy-2-methoxymethyl-2-methyl-N-(3-oxo-propyl)-propionamide

To a solution of 3 g of N-(3,3-diethoxy-propyl)-3-methoxy-2-methoxymethyl-2-methyl-propionamide in 71 mL of acetone was added 3.91 g of $TsOH.H_2O$. The mixture was stirred over night at rt, quenched with sat.-$NaHCO_3$ and extracted with DCM. The organic phase was washed with brine, dried over anh. $Na_2SO_4$ and concentrated in vacuo. The resulting crude material was purified by CC using Hept/EtOAc from 100/0 to 0/100 as eluant to yield 2.19 g of 3-methoxy-2-methoxymethyl-2-methyl-N-(3-oxo-propyl)-propionamide LC-MS: $t_R$=0.52/0.67 min; $[M+H]^+$: 218.35.

1.3 Toluene-4-sulfonic acid 2-((1S,2S)-6-fluoro-2-hydroxy-1-isopropyl-1,2,3,4-tetrahydro-naphthalen-2-yl)-ethyl ester To a mixture of 30 g of (1S,2S)-6-fluoro-2-(2-hydroxyethyl)-1-isopropyl-1,2,3,4-tetrahydro-naphthalen-2-ol (prepared as described in EP 177960), 0.20 mL of $NEt_3$ and 2.9 g of DMAP in 240 mL toluene was added 24.9 g of Ts-$C_1$ at 5° C. and the mixture was stirred overnight at rt. The reaction mixture was quenched with ice-water and extracted with ether. The organic phase was washed with 2M-HCl and sat.-$NaHCO_3$, dried ($Na_2SO_4$) and concentrated in vacuo. The residue was purified by recrystallisation from Hept to yield 41.4 g of toluene-4-sulfonic acid 2-((1S,2S)-6-fluoro-2-hydroxy-1-isopropyl-1,2,3,4-tetrahydro-naphthalen-2-yl)-ethyl ester as white solid.

LC-MS: $t_R$=1.08 min; $[M-H_2O+H]^+$: 389.20.

1.4 (1S,2S)-6-Fluoro-1-isopropyl-2-(2-methylamino-ethyl)-1,2,3,4-tetrahydro-naphthalen-2-ol 8 g of toluene-4-sulfonic acid 2-((1S,2S)-6-fluoro-2-hydroxy-1-isopropyl-1,2,3,4-tetrahydro-naphthalen-2-yl)-ethyl ester were dissolved in a 8 M solution of $MeNH_2$ in EtOH (100 mL). The mixture was stirred overnight in at 40° C., diluted with DCM and washed with sat.-$NaHCO_3$. The organic phase was dried over anh. $Na_2SO_4$ and concentrated to give 5.29 g of (1S,2S)-6-fluoro-1-isopropyl-2-(2-methylamino-ethyl)-1,2,3,4-tetrahydro-naphthalen-2-ol as beige solid.

LC-MS: $t_R$=0.75 min; $[M+H]^+$: 266.41.

1.5 N-(3-{[2-((1S,2S)-6-Fluoro-2-hydroxy-1-isopropyl-1,2,3,4-tetrahydro-naphthalen-2-yl)-ethyl]-methyl-amino}-propyl)-3-methoxy-2-methoxymethyl-2-methyl-propionamide 6.55 g of (1S,2S)-6-fluoro-1-isopropyl-2-(2-methylamino-ethyl)-1,2,3,4-tetrahydro-naphthalen-2-ol were dissolved in DCM (138 mL)/AcOH (15 mL). 5.36 g of 3-methoxy-2-methoxymethyl-2-methyl-N-(3-oxo-propyl)-propionamide and 6.39 g of sodium cyanoborohydride were added. The reaction mixture was stirred for 2 h at room temperature, quenched with sat.-$NaHCO_3$ and extracted with DCM. The organic phase was washed with brine, dried over anh. $Na_2SO_4$ and concentrated in vacuo. The resulting crude material was purified by CC using DCM/MeOH/$NEt_3$ from 100/0/1 to 40/1/0.4 as eluant to yield 10.57 g of N-(3-{[2-((1S,2S)-6-Fluoro-2-hydroxy-1-isopropyl-1,2,3,4-tetrahydro-naphthalen-2-yl)-ethyl]-methyl-amino}-propyl)-3-methoxy-2-methoxymethyl-2-methyl-propionamide as amber resin.

LC-MS: $t_R$=0.82 min; $[M+H]^+$: 467.51.

1.6 (1S,2S)-6-Fluoro-1-isopropyl-2-(2-{[3-(3-methoxy-2-methoxymethyl-2-methyl-propylamino)-propyl]-methyl-amino}-ethyl)-1,2,3,4-tetrahydro-naphthalen-2-ol To a solution of 4.09 g of N-(3-{[2-((1S,2S)-6-fluoro-2-hydroxy-1-isopropyl-1,2,3,4-tetrahydro-naphthalen-2-yl)-ethyl]-methyl-amino}-propyl)-3-methoxy-2-methoxymethyl-2-methyl-propionamide in anh. THF (70 mL) was added dropwise at 0° C. for 15 min a 1M solution of borane-THF complex in THF (87 mL). The mixture was stirred for 25 min at rt then for 1.5 h at 65° C. It was cooled down to 0° C., quenched with 1M-NaOH and extracted with DCM. The organic phase was dried over anh. $Na_2SO_4$ and concentrated in vacuo. The resulting crude as borane complex was dissolved in MeOH (60 mL) and treated with ethylene diamine (2.37 mL) under microwave conditions (120° C. for 180 s). The mixture was concentrated in vacuo and the resulting residue was taken up in DCM. The organic phase was washed with brine, dried over anh. $Na_2SO_4$ and concentrated in vacuo. The oily crude was purified by CC using EtOAc/MeOH/$NEt_3$ from 95/5/1 to 60/40/1 as eluant to yield 2.74 g of (1S,2S)-6-fluoro-1-isopropyl-2-(2-{[3-(3-methoxy-2-methoxymethyl-2-methyl-propylamino)-propyl]-methyl-amino}-ethyl)-1,2,3,4-tetrahydro-naphthalen-2-ol as yellowish oil.

LC-MS: $t_R$=0.73 min; $[M+H]^+$: 453.38.

1.7 2-Fluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide To a solution of 2.73 g of (1S,2S)-6-fluoro-1-isopropyl-2-(2-{[3-(3-methoxy-2-methoxymethyl-2-methyl-propylamino)-propyl]-methyl-amino}-ethyl)-1,2,3,4-tetrahydro-naphthalen-2-ol in DCM (29 mL) was added at 0° C., 1.5 mL of DIPEA and 1.1 mL of fluoroacetyl chloride. The mixture was stirred for 20 min at 0° C. then allowed to warm up to rt for 1 h and quenched with sat.-$NaHCO_3$. The organic phase was dried over anh. $Na_2SO_4$ and concentrated in vacuo. The resulting crude ester was dissolved in EtOH (29 mL) and treated with 15 mL of a 1M NaOH solution. The mixture was stirred for 15 min at rt and concentrated in vacuo. The resulting residue was taken up in DCM and washed with sat.-$NaHCO_3$ and brine. The organic phase was dried over anh. $Na_2SO_4$ and concentrated in vacuo. The resulting crude was purified by CC using EtOAc/MeOH/$NEt_3$ from 100/0/1 to 90/10/1 to yield 2.07 g of 2-fluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide as orange oil.

LC-MS: $t_R$=0.85 min; $[M+H]^+$: 513.40.

1.8 (1S,2S)-6-Fluoro-2-[2-({3-[2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol To a solution of 2.24 g of 2-fluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide in anh. THF (35 mL) was added dropwise at 0° C. for 20 min a 1M solution of borane-THF complex in THF (44 mL). The mixture was stirred for 10 min at rt then for 1.5 h at 65° C. It was cooled down to 0° C., quenched with 1M-NaOH and extracted with DCM. The organic phase was dried over anh. $Na_2SO_4$ and concentrated in vacuo. The resulting crude as borane complex was dissolved in MeOH (42 mL) and treated with ethylene diamine (1.18 mL) under microwave conditions (120° C. for 180 s). The mixture was concentrated in vacuo and the resulting residue was taken up in DCM. The organic phase was washed with brine, dried over anh. $Na_2SO_4$ and concentrated in vacuo. The oily crude was purified by CC using EtOAc/MeOH/$NEt_3$ from 100/0/1 to 92/8/1 as eluant to yield 1.51 g of (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol as yellowish oil.

LC-MS: $t_R$=0.75 min; $[M+H]^+$: 499.41.

Example 2

Isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester

2.1 Isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester To a solution of 398 mg of (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol and 0.44 mL of $NEt_3$ in 8 mL of DCM 0.25 mL of isobutyrylchloride was added at 0° C. The mixture was stirred for 25 min at 0° C. and then for 3 h at rt. It was quenched with sat. aqueous $NaHCO_3$ and extracted with DCM. The organic phase was dried over anh. $Na_2SO_4$ and concentrated in vacuo. The resulting crude was purified by CC using EtOAc/Hept 3/1 as eluant to yield 411 mg of isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester as orange oil.

LC-MS: $t_R$=0.90 min; $[M+H]^+$: 569.32.

2.2 Isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester dihydrochloride salt The above product may be transformed into the corresponding dihydrochloride salt using the following procedure.

411 mg of isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester were dissolved in 10 mL EtOAc, the solution was cooled with an ice bath and 2.4 mL of 3M HCl in EtOAC were added. The reaction mixture was evaporated to dryness without heating to give the desired isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester dihydrochloride salt.

Example 3

3,3,3-Trifluoro-propionic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester This compound was prepared using a method analogous to that of example 2, step 2.1, 3,3,3-trifluoropropionyl chloride replacing isobutyrylchloride, except that no NEt$_3$ was used and that the reaction mixture was stirred for 1 h at 0° C.

LC-MS: $t_R$=0.84 min; [M+H]$^+$: 609.35.

Example 4

Fluoro-acetic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester This compound was prepared using a method analogous to that of example 2, step 2.1, fluoroacetyl chloride replacing isobutyrylchloride except that no NEt$_3$ was used.

LC-MS: $t_R$=0.81 min; [M+H]$^+$: 559.28.

Example 5

(1S,2S)-2-[2-({3-[(2,2-Difluoro-ethyl)-(3-methoxy-2-methoxymethyl-2-methyl-propyl)-amino]-propyl}methyl-amino)-ethyl]-6-fluoro-1-isopropyl-1,2,3,4-tetrahydro-naphthalen-2-ol 5.1 2,2-Difluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide To a solution of 1 g of (1S,2S)-6-fluoro-1-isopropyl-2-(2-{[3-(3-methoxy-2-methoxymethyl-2-methyl-propylamino)-propyl]-methyl-amino}-ethyl)-1,2,3,4-tetrahydro-naphthalen-2-ol in DCM (11 mL)/pyridine (11 mL) was added at 0° C., 0.77 mL of difluoroacetic anhydride. The mixture was stirred for 45 min at 0° C. then allowed to warm up to rt and stirred for 5 h. It was diluted with DCM and washed with sat.-NaHCO$_3$. The organic phase was dried over anh. Na$_2$SO$_4$ and concentrated in vacuo. The resulting crude was purified by CC using EtOAc/Hept/NEt$_3$ from 1/2/0.03 to yield 818 mg of 2,2-difluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide as yellowish resin.

LC-MS: $t_R$=0.90 min; [M+H]$^+$: 531.33

5.2 (1S,2S)-2-[2-({3-[(2,2-Difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-ol This compound was prepared using a method analogous to that of example 1, step 1.8, intermediate 5.1 replacing intermediate 1.7.

LC-MS: $t_R$=0.93 min; [M+H]$^+$: 517.34

Example 6

Isobutyric acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester This compound was prepared using a method analogous to that of example 2, step 2.1, intermediate 5.2 replacing intermediate 1.8.

LC-MS: $t_R$=1.07 min; [M+H]$^+$: 587.54

Example 7

3,3,3-Trifluoro-propionic acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester This compound was prepared using a method analogous to that of example 2, step 2.1, intermediate 5.2 replacing intermediate 1.8 and 3,3,3-trifluoropropionyl chloride replacing isobutyrylchloride. As a slight modification, the reaction mixture was only stirred at 0° C. and no NEt$_3$ was used.

LC-MS: $t_R$=1.07 min; [M+H]$^+$: 627.30

Example 8

(1S,2S)-6-Fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-ol 8.1 2,2,2-Trifluoro-N-(3-{[2-((1S,2S)-6-fluoro-2-hydroxy-1-isopropyl-1,2,3,4-tetrahydro-naphthalen-2-yl)-ethyl]-methyl-amino}-propyl)-N-(3-methoxy-2-methoxymethyl-2-methyl-propyl)-acetamide This compound was prepared using a method analogous to that of example 5, step 5.1, trifluoroacetic anhydride replacing difluoroacetic anhydride.

LC-MS: $t_R$=0.93 min; [M+H]$^+$: 549.32

8.2 (1S,2S)-6-Fluoro-1-isopropyl-2-[2-({3-[3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-ol This compound was prepared using a method analogous to that of example 1, step 1.8, intermediate 8.1 replacing intermediate 1.7.

LC-MS: $t_R$=0.97 min; [M+H]$^+$: 535.33

Example 9

Isobutyric acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester This compound was prepared using a method analogous to that of example 2, step 2.1, intermediate 8.2 replacing intermediate 1.8.

LC-MS: $t_R$=1.09 min; [M+H]$^+$: 605.37

Example 10

3,3,3-Trifluoro-propionic acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester This compound was prepared using a method analogous to that of example 2, step 2.1, intermediate 8.2 replacing intermediate 1.8 and 3,3,3-trifluoropropionyl chloride replacing isobutyrylchloride. As a slight modification, the reaction mixture was only stirred at 0° C. and no NEt$_3$ was used.

LC-MS: $t_R$=1.09 min; [M+H]$^+$: 645.37

Biological Tests

In Vitro Assay L Channel

The L channel antagonistic activity (IC$_{50}$ values) of the compounds of formula (I) is determined in accordance with the following experimental method.

Human embryonic kidney (HEK293) cells expressing the human Ca$_v$1.2 channel in addition to the auxiliary subunits β-2a and α2δ-1, are grown in culture medium (DMEM containing 10% heat-inactivated fetal calf serum (FCS), 100 U/ml penicillin, 100 μg/ml streptomycin, 100 μg/ml G418, 40 μg/ml zeocin and 100 μg/ml hygromycin). The cells are seeded at 20.000 cells/well into 384-well black clear bottom sterile plates (poly-L-lysine-coated, Becton Dickinson). The seeded plates are incubated overnight at 37° C. in 5% CO$_2$. The KCl solution is prepared as 80 mM stock solution in assay buffer (HBSS containing 0.1% BSA, 20 mM HEPES, 0.375 g/l NaHCO$_3$, adjusted to pH 7.4 with NaOH) for use in the assay at a final concentration of 20 mM. Antagonists are prepared as 10 mM stock solutions in DMSO, then diluted in 384 w plates first in DMSO, then in assay buffer to obtain 3× stocks. On the day of the assay, 25 μl of staining buffer (HBSS containing 20 mM HEPES, 0.375 g/l NaHCO$_3$, and 3 μM of the fluorescent calcium indicator fluo-4 AM (1 mM stock solution in DMSO, containing 10% pluronic) is added to each well of the seeded plate. The 384-well cell-plates are incubated for 60 min at 37° C. in 5% CO$_2$ followed by washing with 2×50 μl per well using assay buffer leaving 50 μl/well of this buffer for equilibration at room temperature (30-60 min). Within the Fluorescent Imaging Plate Reader (FLIPR, Molecular Devices), antagonists are added to the plate in a volume of 25 μl/well, incubated for 3 min and finally 25 μl/well of KCl solution is added for cellular depolarization. Fluorescence is measured for each well at 2 second intervals for 8 minutes, and the area under the curve of each fluorescence peak is compared to the area of the fluorescence peak induced by 20 mM KCl with vehicle in place of antagonist. For each antagonist, the IC$_{50}$ value (the concentration (in nM) of compound needed to inhibit 50% of the KCl-induced fluorescence response) up to 10 μM is determined. The calculated IC$_{50}$ values of the compounds may fluctuate depending on the daily cellular assay performance. Fluctuations of this kind are known to those skilled in the art.

IC$_{50}$ values all example compounds are in the range of 383 to 1837 nM with an average of 764 nM in this assay.

In Vitro Assay T Channel:

The T channel antagonistic activity (IC$_{50}$ values) of the compounds of formula (I) is determined in accordance with the following experimental method and data are shown in Table 1.

Human embryonic kidney (HEK293) cells expressing the human Ca$_v$3.1 Ca$_v$3.2 or Ca$_v$3.3 channel, respectively, are grown in culture medium (DMEM containing 10% heat-inactivated fetal calf serum (FCS), 100 U/ml penicillin, 100 μg/ml streptomycin and 1 mg/ml G418). The cells are seeded at 20.000 cells/well into 384-well black clear bottom sterile plates (poly-L-lysine-coated, Becton Dickinson). The seeded plates are incubated overnight at 37° C. in 5% CO$_2$. The Ca$^{2+}$ solution is prepared as 100 mM stock solution in 100 mM tetraethylammoniumchloride (TEA-chloride), 50 mM HEPES, 2.5 mM CaCl$_2$, 5 mM KCl, 1 mM MgCl$_2$, adjusted to pH 7.2 with TEA-hydroxide, for use in the assay at a final concentration of 10 mM. Antagonists are prepared as 10 mM stock solutions in DMSO, then diluted in 384 w plates first in DMSO, then in 100 mM TEA-chloride, 50 mM HEPES, 2.5 mM CaCl$_2$, 5 mM KCl, 1 mM MgCl$_2$, adjusted to pH 7.2 with TEA-hydroxide, to obtain 9× stocks. On the day of the assay, 25 μl of staining buffer (HBSS containing 20 mM HEPES, 0.375 g/l NaHCO$_3$ and 3 μM of the fluorescent calcium indicator fluo-4 AM (1 mM stock solution in DMSO, containing 10% pluronic) is added to each well of the seeded plate. The 384-well cell-plates are incubated for 60 min at 37° C. in 5% CO$_2$ followed by washing with 2×50 μl per well using HBSS containing 0.1% BSA, 20 mM HEPES, 0.375 g/l NaHCO$_3$, leaving 50 Owen of this buffer for equilibration at room temperature (30-60 min). Within the Fluorescent Imaging Plate Reader (FLIPR, Molecular Devices), antagonists are added to the plate in a volume of 6.25 Owen, incubated for 3 min, and finally 6.25 Owen of Ca$^{2+}$ solution is added. Fluorescence is measured for each well at 2 second intervals for 8 minutes, and the area under the curve of each fluorescence peak is compared to the area of the fluorescence peak induced by 10 mM Ca$^{2+}$ with vehicle in place of antagonist. For each antagonist, the IC$_{50}$ value (the concentration (in nM) of compound needed to inhibit 50% of the Ca$^{2+}$-induced fluorescence response) up to 10 μM is determined. The calculated IC$_{50}$ values of the compounds may fluctuate depending on the daily cellular assay performance. Fluctuations of this kind are known to those skilled in the art.

TABLE 1

| Compound of Example | IC$_{50}$ [nM] | Compound of Example | IC$_{50}$ [nM] | Compound of Example | IC$_{50}$ [nM] |
|---|---|---|---|---|---|
| 1 | 3252 (n = 2) | 2 | 3146 (n = 4) | 3 | 5406 (n = 3) *[1] |
| 4 | 3961 (n = 2) | 5 | 3701 (n = 2) | 6 | 7889 (n = 2) |
| 7 | 6343 (n = 2) *[2] | 8 | 2879 (n = 2) | 9 | 1694 (n = 1) *[1] |
| 10 | >10000 (n = 4) | | | | |

IC$_{50}$ values are expressed as geometric mean from n values;
*[1] in addition, compound measured once with IC$^{50}$ > 10000 nM;
*[2] in addition, compound measured twice with IC$^{50}$ > 10000 nM.

Effect on Isolated Hearts According to the Langendorff Method (Lgdff)

The compounds were tested for their potential to reduce blood pressure and their effect on the contractility of the heart muscle. EC$_{50}$ values on isolated mouse hearts were determined according to Literature (Doring H J., The isolated perfused heart according to Langendorff technique—function—application, Physiol. Bohemoslov. 1990, 39(6), 481-504; Kligfield P, Horner H, Brachfeld N., A model of graded ischemia in the isolated perfused rat heart, J. Appl. Physiol. 1976 June, 40(6), 1004-8).

7 example compounds have been measured using the procedure described above for the Langendorff experiment. The measured EC$_{50}$ values were in the range of 7 to 29 nM with an average of 13 nM. Results for selected compounds are given in table 2.

TABLE 2

| Compound of Example | EC$_{50}$ [nM] | Compound of Example | EC$_{50}$ [nM] | Compound of Example | EC$_{50}$ [nM] |
| --- | --- | --- | --- | --- | --- |
| 3 | 7 | 6 | 9 | 10 | 9 |

The invention claimed is:

1. A compound of formula (I)

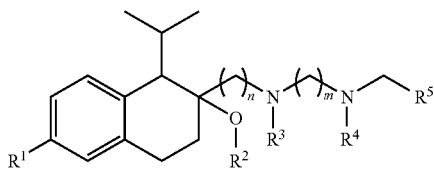

Formula (I)

wherein
R$^1$ represents hydrogen or fluorine;
R$^2$ represents hydrogen, or —CO—R$^{21}$;
R$^{21}$ represents (C$_{1-5}$)alkyl, (C$_{1-3}$)fluoroalkyl, (C$_{3-6}$)cycloalkyl, (C$_{3-6}$)cycloalkyl-(C$_{1-3}$)alkyl, (C$_{1-5}$)alkoxy, (C$_{1-2}$)alkoxy-(C$_{1-3}$)alkyl, or R$^{22}$R$^{23}$N—;
R$^{22}$ represents (C$_{1-5}$)alkyl;
R$^{23}$ represents hydrogen, or (C$_{1-5}$)alkyl;
n represents the integer 1, 2, 3, or 4;
m represents the integer 2, 3, 4, or 5;
R$^3$ represents hydrogen, (C$_{1-5}$)alkyl, or (C$_{1-3}$)fluoroalkyl;
R$^4$ represents (C$_{1-3}$)fluoroalkyl which is optionally mono-substituted with phenyl;
R$^5$ represents (C$_{1-5}$)alkyl, which is unsubstituted, mono-, or di-substituted, wherein each substituent is independently selected from the group consisting of hydroxy, (C$_{1-2}$)alkoxy, (C$_{1-2}$)alkoxy-(C$_{1-3}$)alkoxy, hydroxy-(C$_{2-4}$)alkoxy, aryl-(C$_{1-3}$)alkoxy, and aryl-(C$_{1-2}$)alkoxy-(C$_{1-3}$)alkoxy;
or R$^5$ represents (C$_{1-5}$)alkyl, which is di-substituted, wherein one substituent is (C$_{1-2}$)alkoxy and the other is phenyl;
or R$^5$ represents a saturated four- to eight-membered carbon ring optionally containing two oxygen ring atoms, whereby the two oxygen ring atoms are not adjacent to each other;
in a free or a salt form.

2. The compound according to claim 1, wherein the configuration of the tetrahydronaphthalene moiety is such that the R$^2$—O— substituent and the isopropyl substituent of the tetrahydronaphthalene moiety are in cis relation, in a free or a salt form.

3. The compound according to claim 1, wherein R$^{21}$ represents (C$_{1-5}$)alkyl, or (C$_{1-3}$)fluoroalkyl, in a free or a salt form.

4. The compound according to claim 1, wherein m represents the integer 3, in a free or a salt form.

5. The compound according to claim 1, wherein n represents the integer 2, in a free or a salt form.

6. The compound according to claim 1, wherein R$^3$ represents (C$_{1-4}$)alkyl, in a free or a salt form.

7. The compound according to claim 1, wherein R$^4$ represents unsubstituted (C$_{1-3}$)fluoroalkyl, in a free or a salt form.

8. The compound according to claim 1, wherein R$^5$ represents (C$_{1-5}$)alkyl, which is unsubstituted, mono-, or di-substituted, wherein each substituent is independently selected from the group consisting of hydroxy, (C$_{1-2}$)alkoxy, (C$_{1-2}$)alkoxy-(C$_{1-3}$)alkoxy, and hydroxy-(C$_{2-4}$)alkoxy; or R$^5$ represents a saturated four- to eight-membered carbon ring containing two oxygen ring atoms, whereby the two oxygen ring atoms are not adjacent to each other, in a free or a salt form.

9. The compound according to claim 1 selected from the group consisting of
(1S,2S)-6-Fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-ol;
Isobutyric acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
3,3,3-Trifluoro-propionic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
Fluoro-acetic acid (1S,2S)-6-fluoro-2-[2-({3-[(2-fluoro-ethyl)-(3-methoxy-2-methoxymethyl-2-methyl-propyl)-amino]-propyl}-methyl-amino)-ethyl]-1-isopropyl-1,2,3,4-tetrahydro-naphthalen-2-yl ester;
(1S,2S)-2-[2-({3-[(2,2-Difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-ol;
Isobutyric acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester;
3,3,3-Trifluoro-propionic acid (1S,2S)-2-[2-({3-[(2,2-difluoro-ethyl)-(3-methoxy-2-methoxymethyl-2-methyl-propyl)-amino]-propyl}-methyl-amino)-ethyl]-6-fluoro-1-isopropyl-1,2,3,4-tetrahydro-naphthalen-2-yl ester;
(1S,2S)-6-Fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-ol;
Isobutyric acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester; and
3,3,3-Trifluoro-propionic acid (1S,2S)-6-fluoro-1-isopropyl-2-[2-({3-[(3-methoxy-2-methoxymethyl-2-methyl-propyl)-(2,2,2-trifluoro-ethyl)-amino]-propyl}-methyl-amino)-ethyl]-1,2,3,4-tetrahydro-naphthalen-2-yl ester,
in a free or a salt form.

10. A pharmaceutical composition containing, as active principle, a compound of formula (I) according to claim 1, in a free or a pharmaceutically acceptable salt form, and at least one therapeutically inert excipient.

11. A method of treating cardiac ischemia, comprising administering to a subject in need thereof an effective amount of a compound of formula (I) according to claim 1 in a free or a pharmaceutically acceptable salt form.

* * * * *